United States Patent [19]
Kleinschmidt et al.

[11] Patent Number: 4,846,169
[45] Date of Patent: Jul. 11, 1989

[54] DEVICE FOR CONTROLLING RESPIRATING GAS IN AN ANAESTHESIA OR RESPIRATORY APPARATUS

[75] Inventors: Lothar Kleinschmidt, Krummesse; Carl-Friedrich Wallroth; Michael Waschmann, both of Lübeck, all of Fed. Rep. of Germany

[73] Assignee: Drägerwerk Aktiengesellschaft, Lübeck, Fed. Rep. of Germany

[21] Appl. No.: 20,515

[22] Filed: Mar. 2, 1987

[30] Foreign Application Priority Data

Mar. 6, 1986 [DE] Fed. Rep. of Germany ....... 3607320

[51] Int. Cl.$^4$ .............................................. A62B 9/02
[52] U.S. Cl. ............................................... 128/205.24
[58] Field of Search ...................... 128/204.18, 204.29, 128/205.24, 206.15, 207.12, 207.16, 203.13, 203.14, 203.22, 203.25

[56] References Cited

U.S. PATENT DOCUMENTS

| | | | |
|---|---|---|---|
| 3,249,107 | 5/1966 | Delest | 128/204.29 |
| 4,190,045 | 2/1980 | Bartels | 128/205.24 |
| 4,611,591 | 9/1986 | Inui et al. | 128/205.24 |
| 4,694,825 | 9/1987 | Slemmer et al. | 128/205.24 |

FOREIGN PATENT DOCUMENTS

1447091 8/1976 United Kingdom ........... 128/205.24

Primary Examiner—Max Hindenburg
Assistant Examiner—John P. Lacyk
Attorney, Agent, or Firm—Walter Ottesen

[57] ABSTRACT

A device for controlling respirating gas in an anaesthesia or respiratory apparatus contains a multiplicity of control elements. Each control element has a control chamber with control lines and a respirating gas chamber with respiratory gas lines, the control chamber and respirating gas chamber being separated from one another by a closure element. The respirating gas chambers and the control chambers are combined with each other so that as few component parts as possible have to be disassembled and assembled to facilitate cleaning and disinfection. For this purpose, the control chambers are combined into one control block and the respirating gas chambers are combined into one respirating gas block, such that the two blocks can be coupled together into a unit with a common sealing plate defining closure elements. The control chambers and respirating gas chambers are separated and yet are arranged so that the control chambers coact with corresponding ones of the respirating gas chambers.

3 Claims, 2 Drawing Sheets

DEVICE FOR CONTROLLING RESPIRATING GAS IN AN ANAESTHESIA OR RESPIRATORY APPARATUS

FIELD OF THE INVENTION

The invention relates to a device for controlling respirating (breathing) gas in an anaesthesia or respiratory apparatus which contains a multiplicity of control elements each of which has a control chamber with control lines and a respirating gas chamber with respirating gas lines. The control chamber and respirating/gas chamber are separated from one another by a closure element.

BACKGROUND OF THE INVENTION

British Pat. No. 2,062,475 B discloses a pneumatic control system for an anaesthesia respiratory apparatus in which a switchover from automatic respiration to manual respiration and vice versa can be performed by means of a multiple-position valve. For this purpose, the two valves are switched in alternation via an appropriate charge of pressure on the control chamber of the one valve, and the two diaphragm seals of the valves are connected with one another via a common strut. If one valve is open, the other valve is closed, and vice versa. In the pressure chamber of the second valve there is a compression spring, which keeps the diaphragm associated therewith closed as long as no suitable pressure is present in the pressure chamber of the first valve. This kind of valve combination comprises a multiplicity of individual parts, which require a complicated structure and which, when a required cleaning or disinfection of the individual parts that come into contact with respirating gas is performed, necessitate a tedious disassembly and reassembly of these parts.

A further kind of respiratory apparatus is described in published German Patent Application DE-OS No. 33 03 998. Although here a separation between an electronically operating control part and groups of parts that carry respirating gas is sought, nevertheless here again the many valves required are embodied as individual assemblies, and each with all its parts must be disassembled and assembled again for cleaning purposes.

SUMMARY OF THE INVENTION

It is an object of the invention to improve a device for controlling respirating gas in respiratory apparatus of the kind referred to above such that with a multiplicity of control elements, there configuration makes it possible for all the control elements to be freely accessible for cleaning and disinfection purposes by disassembling only a few component parts.

This object is achieved in that the control chambers are combined into a control block and the respirating gas chambers are combined into a respirating gas block such that the two blocks can be coupled together into a unit by means of a common sealing plate having closure elements. In this unit, the control chambers and respirating gas chambers are arranged separately and face one another.

An important advantage of the invention is that because of the modular assembly of the individual blocks, a particularly favorable disposition of the respirating gas lines can be made, so that their large-volume cross sections are readily accessible for cleaning and disinfection. Furthermore, the required number of component parts into which the apparatus must be disassembled for cleaning purposes is reduced to a minimum. The cleaning can be limited to the sealing plate and the lines carrying respirating gas, regardless of how many control chambers or respirating gas chambers are combined in the various blocks. For example, it is necessary only to connect the two blocks by a quick clamping device with which a sealing plate is clamped in place therebetween, the sealing plate being common to all the control elements and having closure elements.

A further advantage is that various blocks can be combined in modular fashion, the ports of control lines and respirating gas lines at the outer faces of the block are connected in a suitable manner as an interface.

According to another feature of the invention, the walls of the respirating gas lines are embodied at least partly by a removable part of the wall of the respirating gas block, the removable wall part being common to the respirating gas lines. As a result, after the wall part is removed, the respirating gas lines are accessible in their full length, so that the effectiveness of cleaning and disinfection can be increased still further.

BRIEF DESCRIPTION OF THE DRAWING

The invention will now be described with reference to the drawings wherein.

DESCRIPTION OF THE PREFERRED EMBODIMENT OF THE INVENTION

Figure 1:
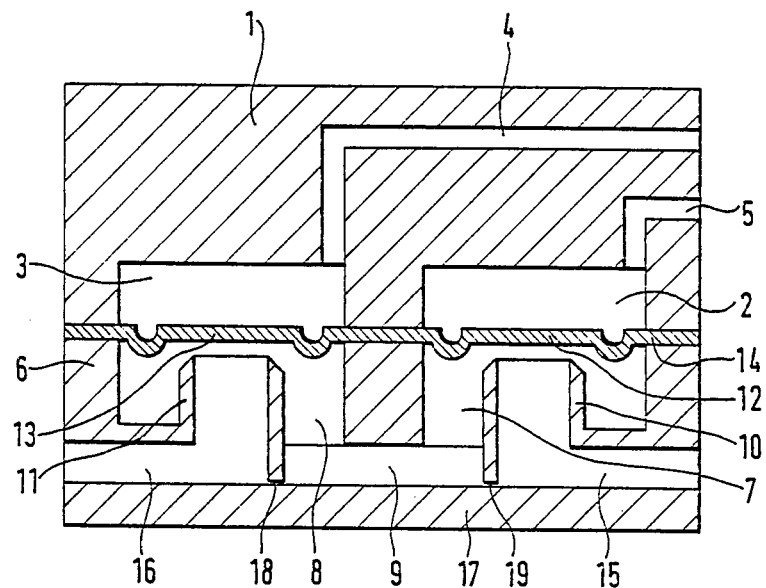
FIG. 1 shows a schematic representation, in section, of an embodiment of the device according to the invention for controlling respirating gas in an anaesthetic or respiratory apparatus.
Figure 2:
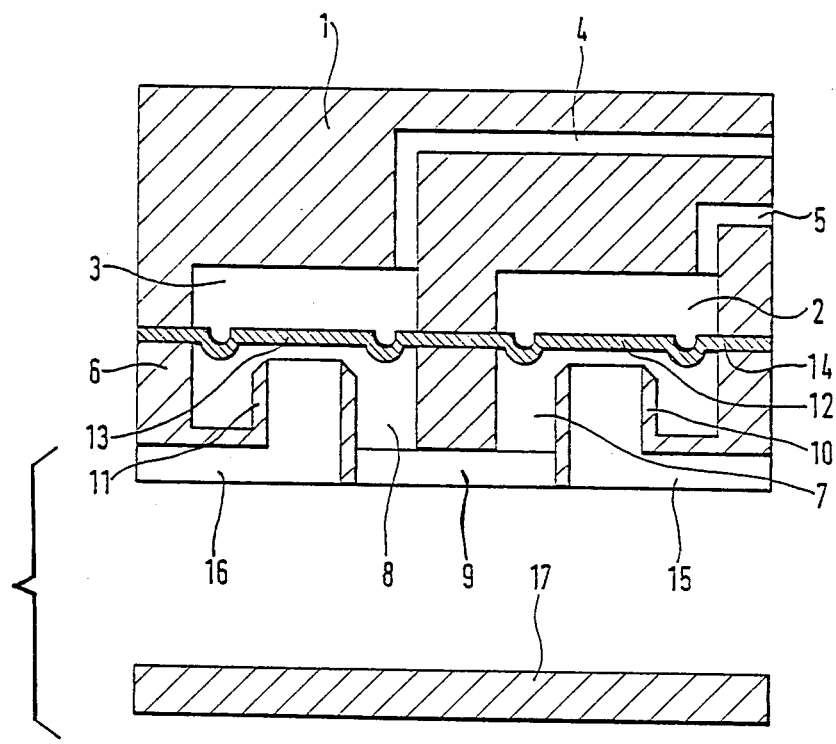
FIG. 2 shows the device of FIG. 1 with the removable wall member separated from the respirating gas block so as to expose the respirating gas lines in their full length and make them accessible for cleaning and disinfection.

The single figure of the drawing is a sectional view of a device for controlling respirating gas and includes a control block 1 in which two control chambers 2 and 3 are located. Control lines 5 and 4 communicate with control chambers 2 and 3, respectively. A respirating gas block 6 contains two respirating gas chambers 7 and 8 which are connected with one another via an outflow line 9. Respirating gas chambers 7 and 8 have corresponding sealing craters 10 and 11, and closure elements 12 and 13 are movable toward these sealing craters, respectively. The closure elements 12 and 13 are connected with one another to define a common sealing plate 14 which is secured between the control block 1 and the respirating gas block 6, for example, with the aid of clamping fasteners (not shown) engaging the outer surfaces of the blocks 1 and 6.

In the embodiment shown, both valves (10, 12) and (11, 13) are shown in the open position, so that respirating gas can flow from the inflow lines 15, 16 through both respiratory gas chambers 7 and 8 and into the outflow line 9. Depending upon the pressure charge filling the control chambers 3 and 2 via the respective control lines 4 and 5 associated therewith, the closure elements 12 and 13 are pressed against the respective sealing craters 10 and 11 and thus effect an interruption of the supply of respirating gas. The wall part 17 facing toward the lines conducting respirating gas can be removed at the partition interfaces 18 and 19, so that free access to the lines carrying respirating gas is possible from this side of the block 6.

In the embodiment shown, the control chambers 2 and 3 are charged with pressure pneumatically via respective control lines 5 and 4. In the same manner, however, component parts that are movable mechanically or via a suitable electric drive means can engage the closure elements 12 and 13 in order to make these elements movable with respect to the sealing craters 10 and 11.

It is understood that the foregoing description is that of the preferred embodiments of the invention and that various changes and modifications may be made thereto without departing from the spirit and scope of the invention as defined in the appended claims.

What is claimed is:

1. A device for controlling respirating gas in an anaesthesia or respiratory apparatus and which must be thoroughly cleaned and disinfected from time to time during use, the device comprising:

a single control block including a plurality of control chambers;

a single respirating gas block separate from said control block and including: a plurality of respirating gas chambers corresponding to respective ones of said control chambers; said respirating gas chambers each having valve seat means in said gas block defining an inlet thereto; and, a plurality of incoming respirating gas lines communicating with corresponding ones of said respirating gas chambers through respective ones of said valve seat means;

said control block and said respirating gas block having respective mutually adjacent interface surfaces conjointly defining a single partition interface space therebetween when placed one next to the other so as to cause said control chambers to the adjacent corresponding ones of said respirating gas chambers thereby defining respective chamber sets;

a single sealing plate common to both of said blocks and disposed in said partition interface space so as to define a single assembly unit with said blocks, said single sealing plate defining a plurality of movable valve closure elements lying in said interface space and being interposed respectively between the control chamber and the respiratory gas chamber of each one of said chamber sets for coacting with respective ones of said valve seat means; said valve closure elements all lying in said interface space and being disposed in said single plate so as to be all immediately and simultaneously accessible for cleaning and disinfection when said plate is removed from said interface space;

said respirating chambers being formed in said respirating block so as to extend downwardly from said interface surface thereof into said respirating block to make all of said chambers likewise immediately and simultaneously accessible for cleaning and disinfection when said control block and said sealing plate are removed from said respirating block;

a plurality of control means arranged in said control block so as to be operatively connected with corresponding ones of said valve closure elements for actuating said valve closure elements independently of each other to open and close said respiratory gas lines to pass and interrupt the flow of respiratory gas therethrough;

said respirating gas block having a planar wall surface facing away from said partition interface space;

said respirating gas lines being respective channels formed in said respirating block so as to extend into said block from said planar wall surface; and, a removable wall member mountable against said planar wall surface to cover over said channels and define a portion of the wall surface of each one of said respirating gas lines when said wall member is in place against said planar wall surface and to uncover and make all of said channels immediately and simultaneously accessible for cleaning and disinfection when said wall member is removed from said respirating block.

2. The device of claim 1, said plurality of control means being a plurality of channels communicating with corresponding ones of said control chambers for conducting a pneumatic charge to actuate said valve closure elements, respectively; said sealing plate coterminous with said blocks and being made of a resilient material so as to permit said valve closure elements to move toward and seal-tight engage said valve seats.

3. A device for controlling respirating gas in an anaesthesia or respiratory apparatus and which must be thoroughly cleaned and disinfected from time to time during use, the device comprising:

a control block including a plurality of control chambers;

a respirating gas block separate from said control block and including: a plurality of respirating gas chambers corresponding to respective ones of said control chambers; said respirating gas chambers each having valve seat means in said gas block defining an inlet thereto; and, a plurality of incoming respirating gas lines communicating with corresponding ones of said respirating gas chambers through respective ones of said valve seat means;

said control block and said respirating gas block having respective manually adajcent planar interface surfaces conjointly defining a single planar partition interface space therebetween when placed one next to the other so as to cause said control chambers to be adjacent corresponding ones of said respirating gas chambers thereby defining respective chamber sets;

a single sealing plate common to both of said blocks and disposed in said partition interface space so as to define a single assembly unit with said blocks and so as to be coterminous therewith, said single sealing plate defining a plurality of movable valve closure elements interposed respectively between the control chamber and the respiratory gas chamber of each one of said chamber sets for coacting with respective ones of said valve seat means; said valve closure elements all lying in said interface space and being disposed in said single plate so as to be all immediately and simultaneously accessible for cleaning and disinfection when said plate is removed from said interface space;

said respirating chambers being formed in said respirating block so as to extend downwardly from said interface surface thereof into said respirating block to make all of said chambers likewise immediately and simultaneously accessible for cleaning and disinfection when said control block and said sealing plate are removed from said respirating block;

said respirating gas lines being formed in said block so as to communicate directly with said respirating chambers; and, a plurality of pneumatic control lines formed entirely within said control block so as to be operatively connected with corresponding ones of said valve closure elements for actuating said valve closure elements independently of each other to open and close said respiratory gas lines to pass and interrupt the flow of respiratory gas therethrough.

* * * * *

UNITED STATES PATENT AND TRADEMARK OFFICE
CERTIFICATE OF CORRECTION

PATENT NO. : 4,846,169
DATED : July 11, 1989
INVENTOR(S) : Lothar Kleinschmidt, Carl-Friedrich Wallroth and Michael Waschmann It is certified that error appears in the above-identified patent and that said Letters Patent is hereby corrected as shown below:

In column 1, line 50: delete "there" and substitute -- their -- therefor.

In column 2, delete line 39 and substitute therefor the following: -- The figures of the drawings are sectional views of -- therefor.

In column 2, line 40: delete "includes" and substitute -- include -- therefor.

In column 3, line 34: delete "the" and substitute -- be -- therefor.

In column 4, line 37: delete "manually adajcent" and substitute -- mutually adjacent -- therefor.

Signed and Sealed this

Eighth Day of May, 1990

*Attest:*

HARRY F. MANBECK, JR.

*Attesting Officer*  *Commissioner of Patents and Trademarks*